United States Patent [19]

Manders et al.

[11] Patent Number: 5,571,179
[45] Date of Patent: Nov. 5, 1996

[54] DIMENSIONALLY ADJUSTABLE SOFT TISSUE EXPANDER AND METHOD

[76] Inventors: Ernest C. Manders; Ernest K. Manders, both of 1 Timberline Pl., Hummelstown, Pa. 17036; Thomas Hooker, 820 Cragmoor Rd., York Haven, Pa. 17370

[21] Appl. No.: 503,621

[22] Filed: Jul. 18, 1995

Related U.S. Application Data

[63] Continuation of Ser. No. 221,104, Mar. 31, 1994, abandoned.

[51] Int. Cl.⁶ ...................................................... A61F 2/12
[52] U.S. Cl. ............................... 623/8; 606/192; 128/899; 623/11
[58] Field of Search ................ 623/8, 11; 606/191–197; 604/96–103, 317, 319, 410; 600/40; 446/180, 226; 128/899

[56] References Cited

U.S. PATENT DOCUMENTS

| | | | |
|---|---|---|---|
| 4,157,085 | 6/1979 | Austad | 128/1 |
| 4,217,889 | 8/1980 | Radovan et al. | 128/1 |
| 4,574,780 | 3/1986 | Manders | 128/1 |
| 4,610,690 | 9/1986 | Tiffany | 623/8 |
| 4,615,704 | 10/1986 | Frisch | 623/8 |
| 4,651,717 | 3/1987 | Jakubczak | 128/344 |
| 4,666,447 | 5/1987 | Smith et al. | 623/8 |
| 4,671,255 | 6/1987 | Dubrul et al. | 128/1 |
| 4,685,447 | 8/1987 | Iversen et al. | 128/1 |
| 4,718,895 | 1/1988 | Kurtz et al. | 604/119 |
| 4,719,918 | 1/1988 | Bonomo et al. | 128/344 |
| 4,731,081 | 3/1988 | Tiffany | 623/8 |
| 4,798,205 | 1/1989 | Bonomo et al. | 128/344 |
| 4,798,578 | 1/1989 | Ranford | 604/4 |
| 4,800,901 | 1/1989 | Rosenberg | 128/899 |
| 4,823,815 | 4/1989 | Watson et al. | 128/897 |
| 4,828,550 | 5/1989 | Heyler, III | 623/8 |
| 4,841,948 | 6/1989 | Bauer et al. | 128/897 |
| 4,841,992 | 6/1989 | Sasaki et al. | 128/899 |
| 4,898,561 | 2/1990 | Nottingham et al. | 446/220 |
| 4,899,764 | 2/1990 | Gauger et al. | 128/899 |
| 4,950,292 | 8/1990 | Audretsch | 623/8 |
| 4,955,395 | 9/1990 | Manders | 623/8 |
| 4,955,907 | 9/1990 | Ledergerber | 623/8 |
| 4,984,585 | 1/1991 | Austad | 128/899 |
| 5,005,591 | 4/1991 | Austad | 128/899 |
| 5,033,481 | 7/1991 | Heyler, III | 623/8 |
| 5,035,349 | 7/1991 | Sasaki et al. | 128/899 |
| 5,066,303 | 11/1991 | Bark et al. | 623/8 |
| 5,074,878 | 12/1991 | Bark et al. | 623/8 |
| 5,083,576 | 1/1992 | Ruiz-Razura et al. | 128/898 |
| 5,092,348 | 3/1992 | Dubrul et al. | 128/899 |
| 5,104,346 | 4/1992 | Smrt | 446/198 |
| 5,109,875 | 5/1992 | Gottlieb | 128/899 |
| 5,133,753 | 7/1992 | Bark et al. | 623/8 |
| 5,141,508 | 8/1992 | Bark et al. | 623/8 |
| 5,146,933 | 9/1992 | Boyd | 128/899 |
| 5,158,571 | 10/1992 | Picha | 623/11 |
| 5,236,454 | 8/1993 | Miller | 623/8 |

FOREIGN PATENT DOCUMENTS 2234902  2/1991  United Kingdom .

OTHER PUBLICATIONS

*Current Therapy in Plastic and Reconstructive Surgery*, "Soft Tissue Expansion", Manders, Mottaleb, Hetzler, 1989, pp. 88–98.
"Tissue Expansion," Instructional Courses, vol. 1, 1988, Mottaleb Wong, Manders, Sasaki, 1988, pp. 277–304.
*Perspectives in Plastic Surgery*, "Case Discussion: Abdominal Wall Reconstruction", Manders & Hurwitz, 1987, pp. 85–94.
*Reconstruction of the Lower Extremity*, "Soft Tissue Expansion in Lower Extremity Reconstruction", Filho, Neves, Gemperli, Kaweski, Kahler, Banducci, Manders, 1991, pp. 593–599.

*Primary Examiner*—Michael J. Milano
*Attorney, Agent, or Firm*—Thomas Hooker, P.C.

[57] ABSTRACT

A soft tissue expander includes a dimensionally adjustable base. The shape of the base is optimally adjusted prior to inserting the expander into an incision formed below a layer of skin to be expanded.

40 Claims, 12 Drawing Sheets

DIMENSIONALLY ADJUSTABLE SOFT TISSUE EXPANDER AND METHOD

This is a continuation of application(s) Ser. No. 08/221,104 filed Mar. 31, 1994 and now abandoned.

FIELD OF THE INVENTION

The invention relates to soft tissue expanders and methods for expanding skin using soft tissue expanders.

DESCRIPTION OF THE PRIOR ART

Conventional soft tissue expanders include a cover and base defining an interior chamber and an inlet port through which liquid may be injected into the chamber to expand the cover above the base. The base is generally flat and has a shape determined during manufacture of the expander. The inlet port may be mounted in the cover or may be external to the expander and connected to the expander by a tube so that injected liquid flows through the tube and into the expander.

Conventional expanders are collapsed and inserted in a surgically formed incisions beneath the layer of skin to be expanded. The pocket may be considerably larger than the expander base to facilitate accurate location of the expander relative to the overlying and adjacent tissue and to assure that the expander base is inserted flat.

After insertion, the incision is closed and the collapsed expander is left in place for a period of time sufficient to allow healing to occur. During healing the incision outside of the expander base closes and holds the base of the collapsed expander in place beneath the layer of skin.

After healing has completed and the expander is stabilized in place, fluid is injected into the expander through the inlet port using a hypodermic needle to force the compliant cover above the base and expand the area of the layer of live skin overlying the cover. The cover is preferably formed from a highly compliant silicone elastomer material which expands during the expansion process. When the expander is collapsed for insertion, the cover may have a greater area than the base and the cover may be folded over itself on top of the base as illustrated and described in Ernest K. Manders U.S. Pat. No. 4,574,780 entitled "Soft Tissue Expander and Method", the disclosure of which is incorporated herein by reference.

Following injection of sufficient liquid into the cavity of the implanted expander and expansion of the overlying skin to a desired extent, the liquid is withdrawn and the expander is collapsed and surgically removed. The expanded tissue flap may be extended to cover an adjacent defect, or may be surgically removed and applied to a remote area of the patient's body.

The shape of the expanded tissue flap is in large part determined by the shape of the expander base. The shapes of bases used in conventional tissue expanders are fixed during manufacture and cannot be varied.

Conventional croissant-shaped expanders have fixed crescent shaped bases. These expanders are used to expand skin adjacent a skin defect so that the expanded skin may be extended to cover the defect. An inventory of different size crescent-shaped expanders, with different size crescent-shaped bases, must be maintained in order to assure that a surgeon has available a proper shaped expander for use in expanding tissue to cover a given size defect.

Conventional expanders do not have adjustable bases. It is conventional for hospitals performing soft tissue expansion to stock inventories of different size expanders having a similar shape but different size bases in order to assure that a surgeon has available an appropriate size expander to meet the requirements of a particular desired soft tissue expansion procedure. Maintenance of the large inventories of expanders is an expensive and undesirable necessity arising from the inability to adjust the shape of bases of conventional expanders.

SUMMARY OF THE INVENTION

The invention is a soft tissue expander formed from an elastomer material and having a highly compliant cover and a dimensionally adjustable base joined to the cover at the peripheral edge of the expander. An inlet port is connected to the cavity formed between the cover and the base. The inlet port may be an external port connected to the expander by a tube or may be an internal port mounted directly in the cover.

The base of the expander includes one or more folds at an edge of the base. The folds may extend completely around the expander or, alternatively, may extend from the base a short distance into the cover. The folds permit a surgeon to adjust the shape of the base of the expander prior to inserting the expander into a surgically-formed incision located below a layer of skin to be expanded. After the incision is closed and heals around the expander, the base is confined in place by surrounding tissue and maintains the shape in which it was inserted throughout the expansion process.

Fluid injected into the expander through the port forces the compliant cover away from the base to expand the overlying skin tissue in a conventional manner. The area of the expanded tissue is determined in large part by the shape given to the base by the surgeon when the expander is inserted into the tissue incision. In this way, the surgeon may adjust the shape of the base of an expander to a desired configuration so that a single expander may be used for a variety of types of expansion procedures without the necessity of maintaining an inventory of specialized expanders for each procedure.

The adjustable expander affords a surgeon the ability to respond to unexpected surgical conditions discovered during surgery. This condition may indicate the procedure requires an expander have a shape different than the shape of the expander initially selected for implantation. In such a case, a surgeon using an adjustable expander can easily adjust the shape of the base of the selected expander. There is no need to use a different expander or to wait unit a different expander is obtained from inventory.

The disclosed adjustable soft tissue expanders include one or more folds extending across the base. In an expander including a pair of opposed tapered arms, the folds permit extension and retraction of the arms and rotation of the arms so that the base of the expander may be moved to assume a crescent shape with the ends of the arms close to each other or the ends of the arms spaced apart from each other. Alternatively, the base may also be shaped to form an elongate base or a relatively short base. Each arm is movable independent of the position of the other arm. This flexibility in shaping the expander base permits the surgeon great flexibility in performing soft tissue expansion procedures and improves the ability to shape an expanded skin layer to meet the needs of a particular patient.

Other objects and features of the invention will become apparent as the description proceeds, especially when taken in conjunction with the accompanying drawings illustrating the invention, of which there are 12 sheets and eight embodiments.

DESCRIPTION OF THE PREFERRED EMBODIMENTS

First Embodiment Expander

The first embodiment adjustable soft tissue expander 10 shown in FIGS. 1–9 is generally crescent-shaped and includes an expandable cover 12 overlying base 14 with the cover and base joined together at peripheral edge 16 to define a fluid tight chamber 18 between the cover and base. A conventional external inlet port 20 is connected to the expander by tube 22 to permit fluid, conventionally a saline solution, to be injected into the chamber 18 or withdrawn from the chamber 18. Fluid is injected or withdrawn by inserting a hypodermic needle into the inlet port 20.

Figure 1:
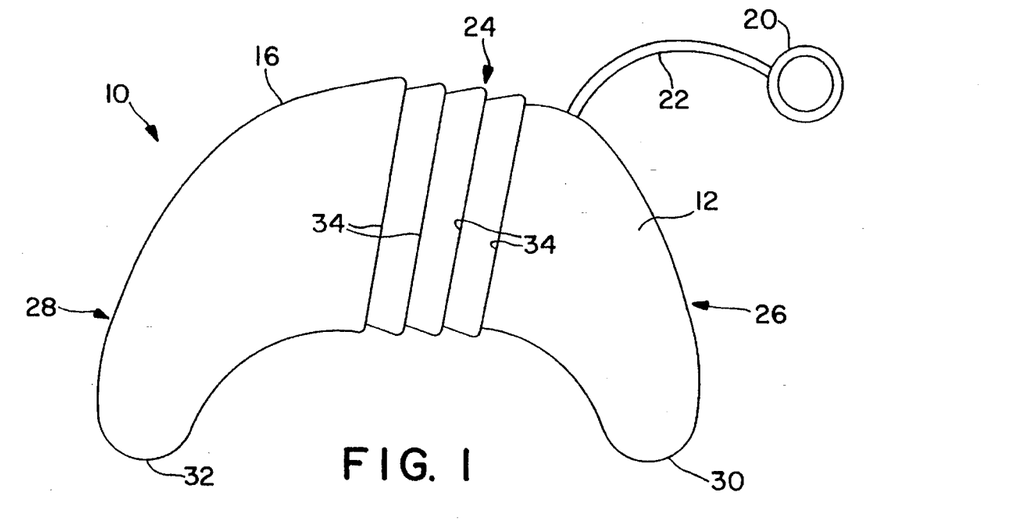
FIG. 1 is a top view of a first embodiment adjustable soft tissue expander.
Figure 2:
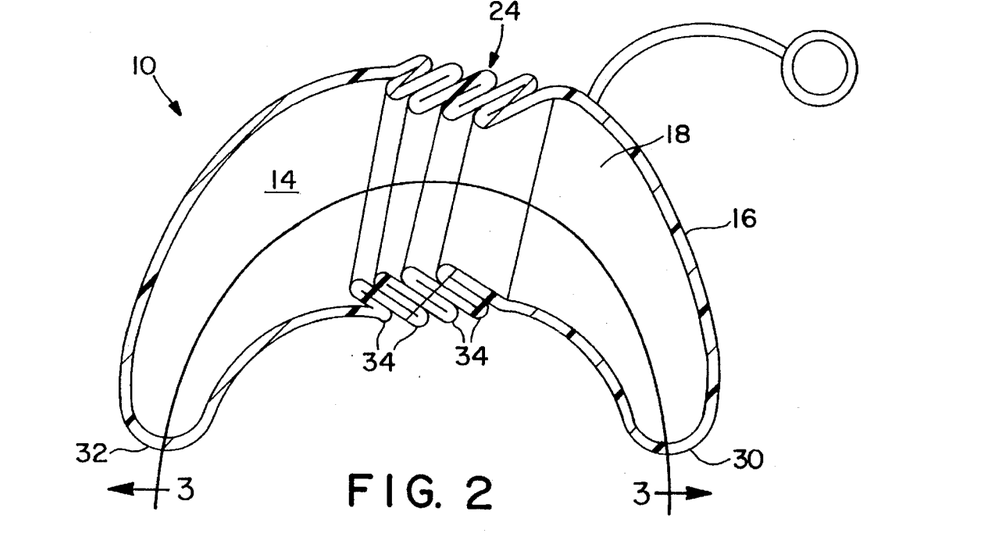
FIG. 2 is a horizontal sectional view taken through the expander of FIG. 1.

The expander includes a tubular central portion 24 and a pair of tubular crescent arms 26 and 28 which are joined to the ends of the tubular central portion. The arms are bent to one side of the tubular portion and are tapered away from the tubular portion to closed ends 30 and 32 located to one side of the central portion.

Figure 25:
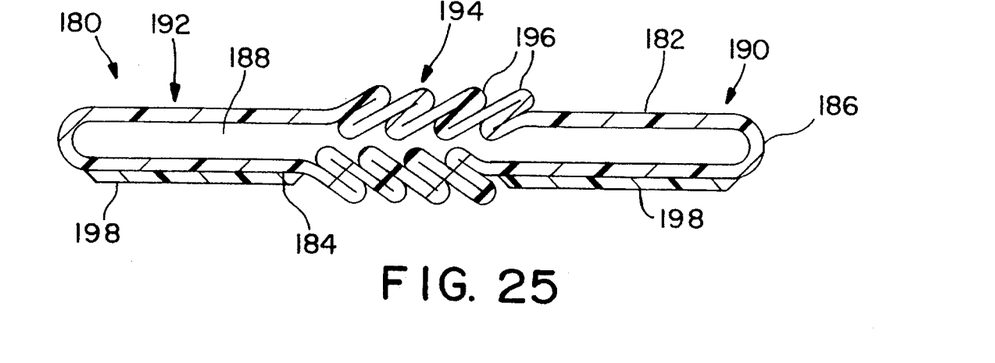
FIG. 25 is a view similar to FIG. 3 showing an eighth embodiment adjustable expander.

The base and cover of the disclosed expanders are preferably formed of a silicone elastomer material. In practice, the covers and bases of the disclosed expanders are considerably thinner than illustrated in the drawings. Preferably, the expander cover is formed of a silicon polymer elastomer having an extension ratio of several hundred percent to permit proper expansion of an overlying skin layer. The base is adjustable in shape. During expansion the base is supported by muscle and bone and does not change shape. FIG. 25 illustrates an expander with a reinforced base. Bases which are not reinforced bow downwardly a short distance into the underlying tissue during expansion.

Figure 3:
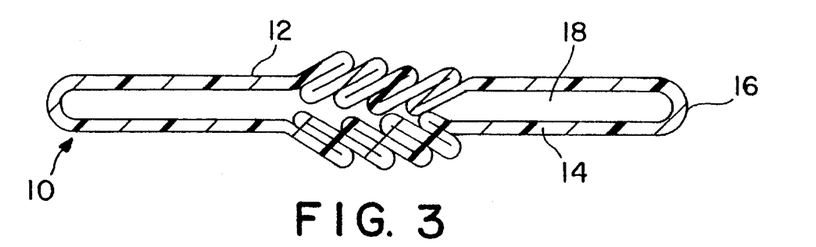
FIG. 3 is a sectional view taken along curved line 3—3 of FIG. 2.

The cover and base of expander 10 at central portion 24 are folded into a plurality of overlapping S-shaped folds 34, each of which extends circumferentially around the cover and base. Folds 34 extend across the width of the base 14 and across the expander cover 12. Each fold 34 includes overlapping layers of elastomer material with adjacent folds joined to each other and folds at the ends of the central portion joining the large dimension ends of arms 26 and 28. Tube 22 opens into the interior chamber 18 through a wall of arm 26 away from the folds 34. If desired, port 20 may be mounted on an arm 26 or 28.

Figure 7:
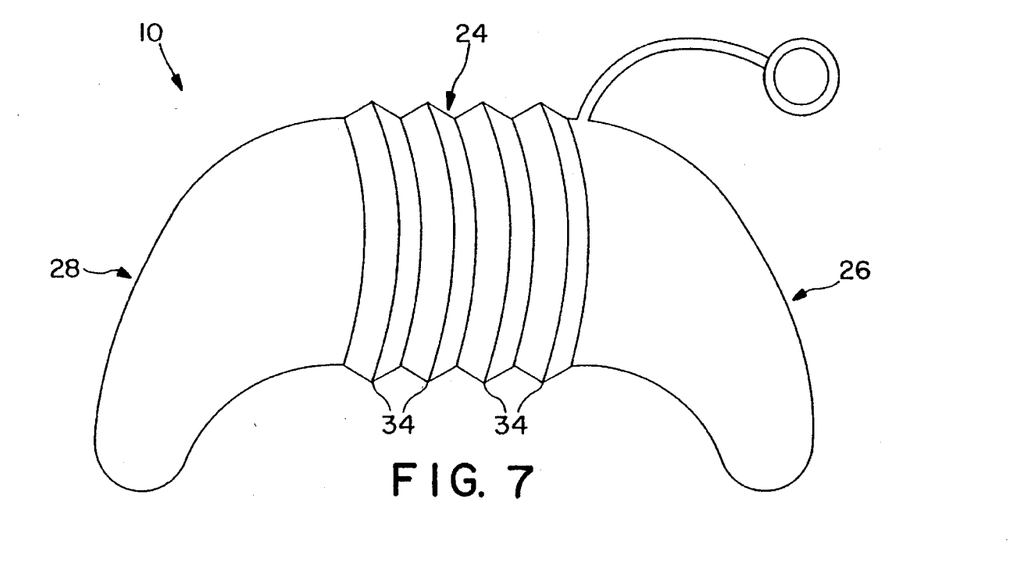
FIGS. 7–9 are views illustrating different positions of the expander of FIG. 1.

The shape of the base of deflated expander 10 is easily adjusted by moving the two arms 26 and 28 to a desired location and allowing the folds in the central portion 24 to correspondingly foreshorten or lengthen as required. For example, FIG. 7 illustrates expander 10 in an elongated position in which the arms 26 and 28 are spaced laterally apart from each other and the folds 34 on the middle portion have been foreshortened to permit separation of the arms. The expander base has been lengthened.

Figure 8:
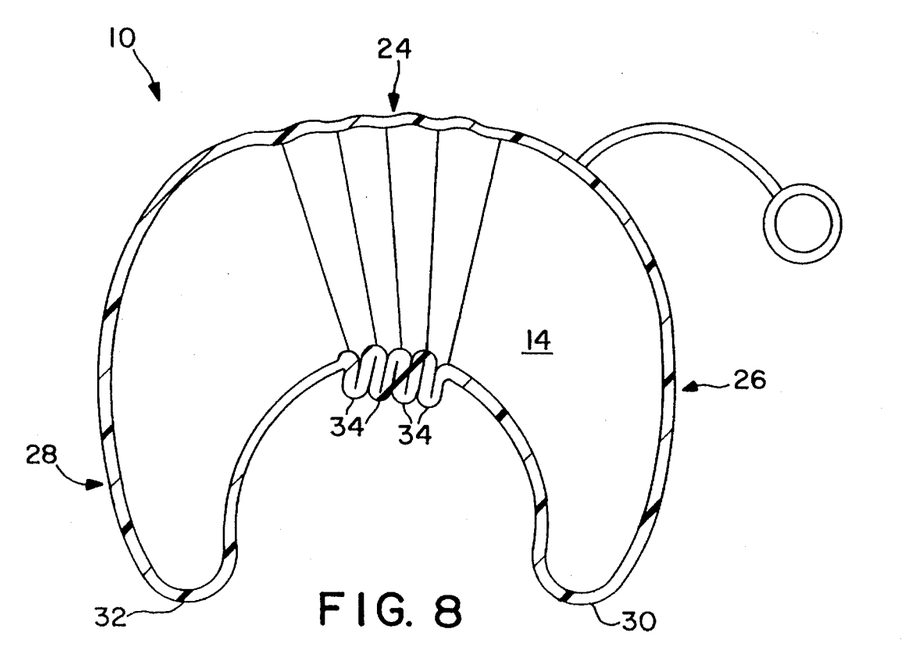

FIG. 8 illustrates a different position of expander base 14 in which the arms 26 and 28 have been rotated toward each other and the folds 34 on the side of the middle portion adjacent arm ends 30 and 32 have been lengthened and the folds on the side of the middle portion away from the arm ends have been foreshortened in order to permit the rotation of the arms. The shape of base 14 has been correspondingly changed, as illustrated.

Figure 9:
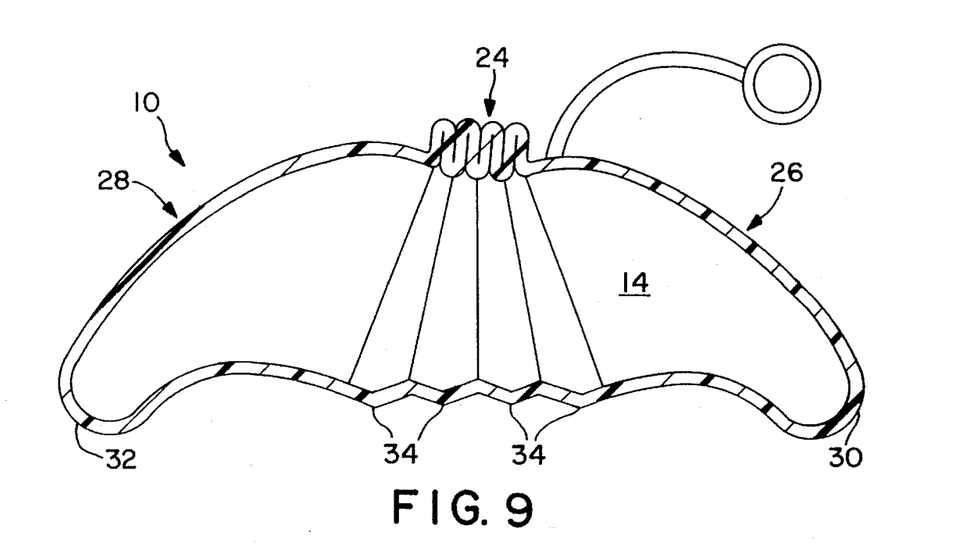

FIG. 9 illustrates the position of expander 10 where the arms 26 and 28 have been rotated in a direction opposite to the direction of rotation illustrated in FIG. 8 to space the arm ends 30 and 32 away from each other and lengthen the folds on the side of the middle portion away from arm ends 30 and 32 and foreshorten the folds on the side of the middle portion adjacent the arm ends.

The folds permit a surgeon to adjust the shape of the expander base so that, when implanted beneath the layer of skin, the base has an optimum shape for the desired tissue expansion. For instance, when it is necessary to form a small expanded skin flat to cover a small defect, the base of expander 10 may be positioned as in FIG. 8 with the arms 30 and 32 located close together to either side of the defect. When expansion is required to form a large flap to cover a larger defect, the expander base may be positioned as in FIG. 2. Expansion of a yet larger flap to cover a yet larger defect may require positioning the expander as shown in FIG. 7. Positioning the expander base as shown in FIG. 9 may also be desirable for other procedures.

Figure 4:
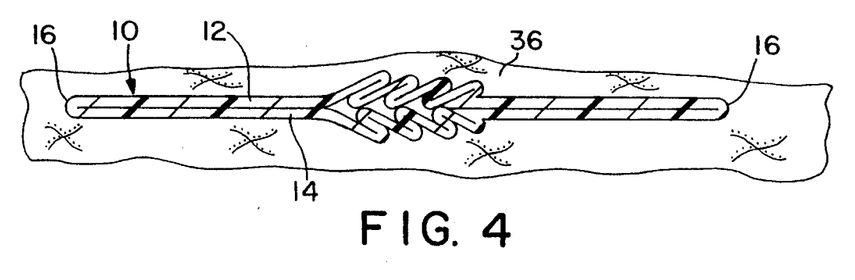
FIGS. 4, 5 and 6 are sectional views showing the expander of FIGS. 1–3 implanted beneath a layer of skin, partially expanded and completely expanded.

FIG. 4 illustrates collapsed expander 10 as shown in FIGS. 1 and 2 implanted in an incision or pocket beneath a soft layer of skin 36. The cover conforms to the shape of the base. The expander base 14 is supported by a layer of muscle or by bone. The folds 34 in the central portion of the expander overlap each other and lie nearly flat on each other at a shallow angle relative to the expander during healing. The folds present a smooth surface to the overlying and underlying tissue. Cover 12 rests flush on base 14. The incision formed prior to insertion of expander 10 below layer 36 is closed or healed around the peripheral edge 16, so that tissue layer 36 is joined to underlying tissue outwardly of the expander edge 16 and the base is held in position in the incision and cannot change shape during expansion. Base 14 is illustrated as being flat. In practice, the base may be curved somewhat to conform to the shape of underlying support tissue.

Figure 5:
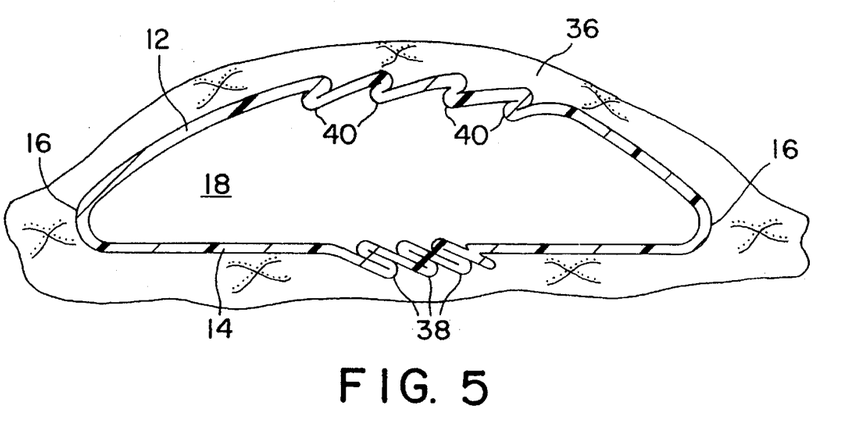

FIG. 5 illustrates partial expansion of expander 10. In this position, sufficient liquid has been injected into the chamber 18 to force the cover 12 upwardly away from the supported base 14 and expand the overlying tissue 36 as shown. During expansion, the folds 38 extending across the base 14 at central portion 24 remain folded in the position assumed when the expander 10 was implanted beneath layer 36 as shown in FIG. 4. During expansion of the cover, the folds 40 extending across the width of the cover at the middle portion between opposite sides of edge 16 are foreshortened as illustrated in FIG. 5.

Figure 6:
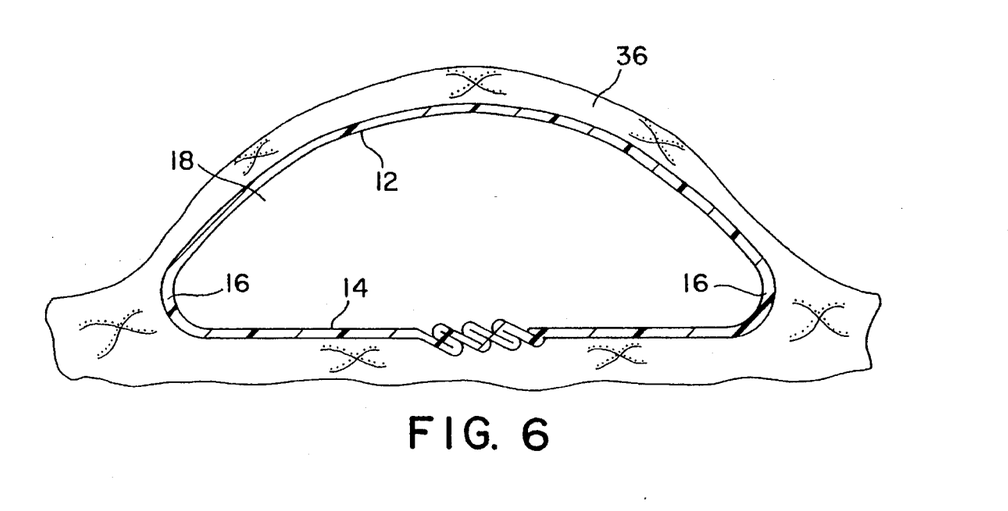

When expander 10 is fully inflated and expansion of the overlying tissue layer 36 is complete, the length of the cover has been increased sufficiently to efface the folds 40, as shown in FIG. 6. Folds 38 extending across the base 14 remain in the inserted position.

After expansion has been completed as shown in FIG. 6, the fluid in chamber 18 is withdrawn through port 20, the expander, port and tube are surgically removed and the expanded tissue layer 36 is advanced or applied over a remote site in accordance with conventional surgical procedures.

Second Embodiment Expander

FIGS. 10–13 illustrate a second embodiment dimensionally adjustable crescent-shaped soft tissue expander 50. Expander 50 is formed from the same material forming expander 10 and includes expandable cover 52, base 54 and peripheral edge 56 joining the cover and base to define an interior chamber 58. Tube 60 connects inlet port 62 to the chamber 58.

Figure 10:
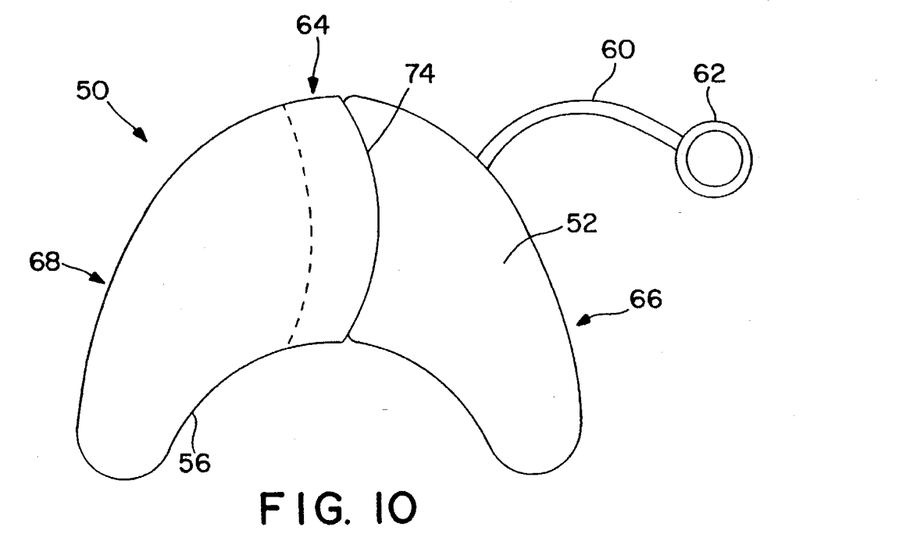
FIG. 10 is a top view of a second embodiment adjustable expander.
Figure 11:
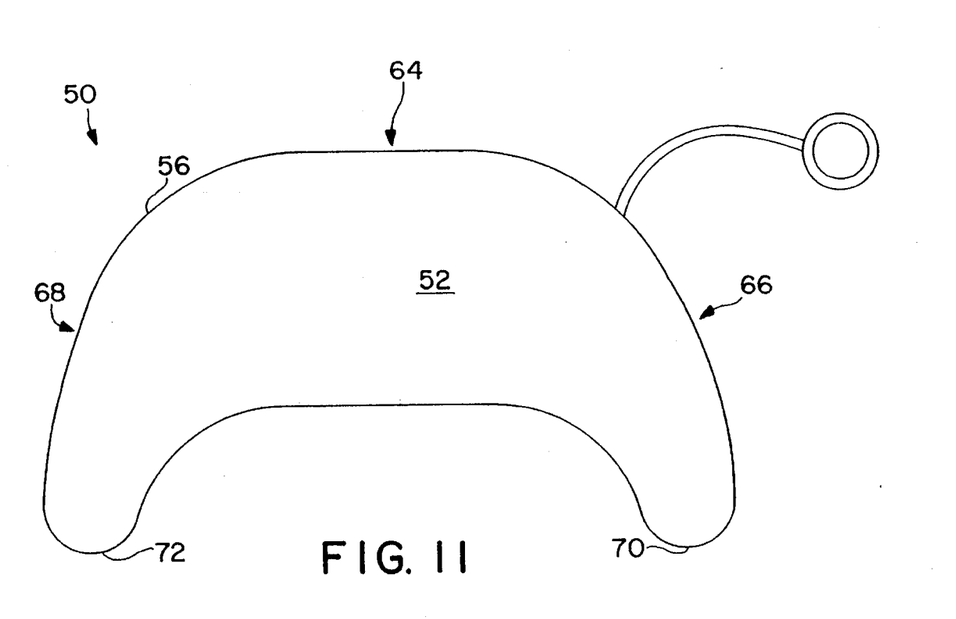
FIG. 11 is a view showing the expander of FIG. 10 in a second elongated position.

Expander 50 includes a tubular central portion 64 and a pair of tubular tapered crescent arms 66 and 68 which join the ends of the central portion as illustrated. The arms include closed narrow ends 70 and 72.

Figure 12:
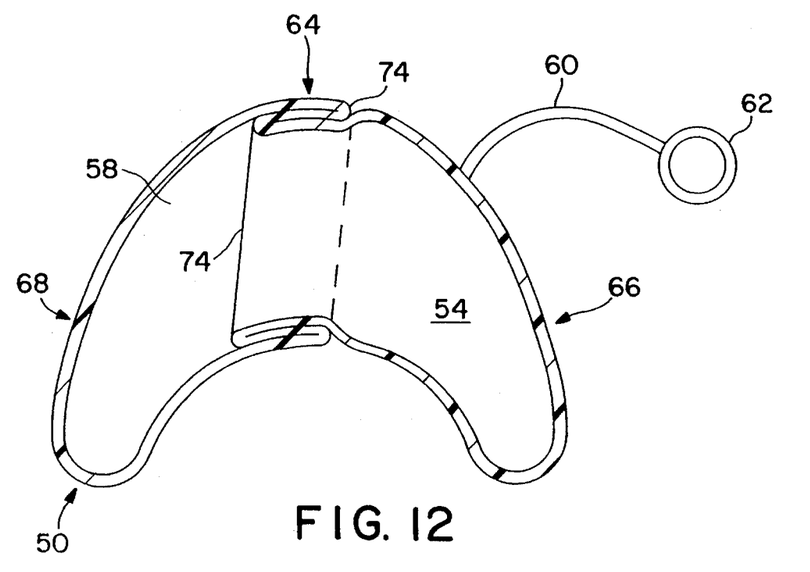
FIGS. 12 and 13 are horizontal sectional views through the expanders of FIGS. 10 and 11, respectively.
Figure 13:
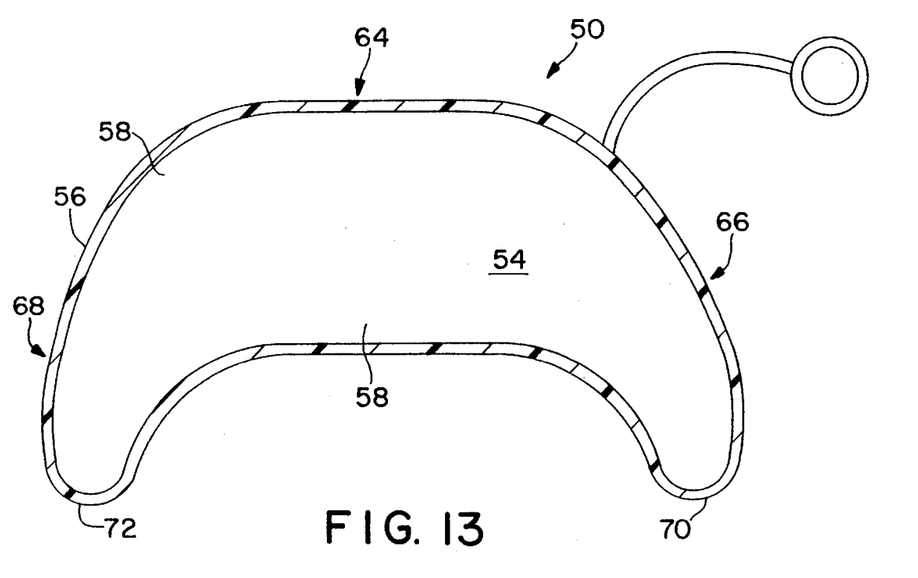

Expander 50 includes a single large circumferential S-shaped fold 74 extending around central portion 64. As shown in FIG. 12, fold 74 includes overlapping layers surrounding the central portion. The fold extends across the width of the base and the cover between opposite sides of edge 56. The fold permits adjustment of the shape of the expander base prior to implantation to accommodate the requirements of a particular surgical procedure. For instance, the arms 66 and 68 of the expander may be moved apart, without rotation, as shown in FIG. 13 to elongate the expander and foreshorten or entirely efface the fold 74 so that the arms are spaced apart. Additionally, fold 74 may be elongated or foreshortened at one side of edge 56 and foreshortened or elongated at the opposite side of edge 56 to permit rotation of the arms 66 and 68 relative to the central portion for adjustment of the shape of base 54 similar to adjustment of base 14 of expander 10.

The adjustability of the shape of base 54 permits a surgeon to implant the expander with the base having an optimum shape for expansion of a particular overlying tissue layer. The cover 52 overlying base 54 conforms to the implanted shape of base 54 and is expanded by the injection of fluid through port 62 and tube 60 into the chamber 58 as described in connection with expansion of expander 10. The arms 66 and 68 may be rotated as required. The arms need not be rotated together or be in symmetrical positions when implanted. Expander 50 assumes a shape similar to the shape of a valise handle when fully elongated as shown in FIG. 13.

Third Embodiment Adjustable Soft Tissue Expander

Figure 14:
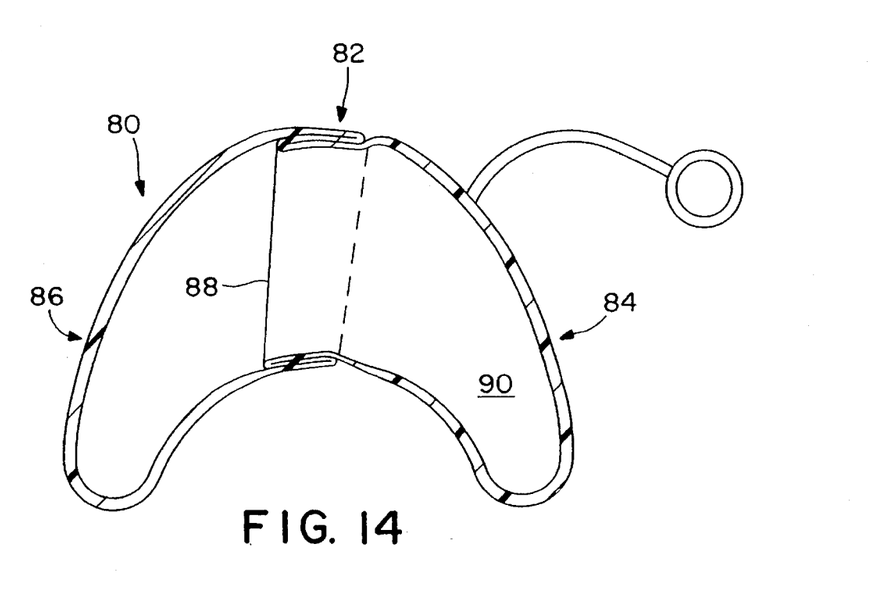
FIGS. 14 and 15, 16 and 17, and 18 and 19 are horizontal sectional views taken through third, fourth and fifth embodiment adjustable tissue expanders.
Figure 15:
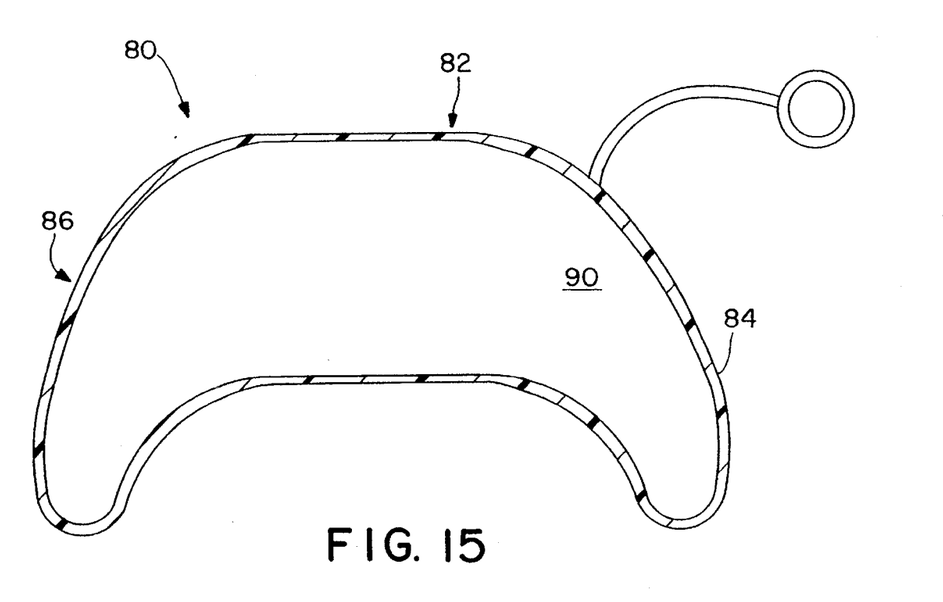

FIGS. 14 and 15 are similar to FIGS. 12 and 13 and illustrate a third embodiment soft tissue expander 80. Expander 80 is identical to expander 50 with the exception that the thickness of the expandable cover and base at middle portion 82 is less than the thickness of the cover and base at arms 84 and 86. A wide, thin tubular S-shaped fold 88 is formed in middle portion 82 and extends across the expander base 90 and overlying cover (not illustrated). The thin central portion has greater flexibility than the thicker arms and permits ready forming of fold 88. Additionally, the thin fold permits greater expansion of the central portion of the cover, which is desirable because the central part of the soft tissue flap must be expanded further than the tissue overlying the arms.

FIG. 15 shows expander 80 in an elongated position in which the arms 84 and 86 are spaced a greater distance apart from each other than in FIG. 14 and the fold 88 has been fully fore-shortened or effaced. In this position, the expander assumes a valise handle shape.

The shape of the base 90 of expander 80 may be adjusted similar to the shapes of the bases of expanders 10 and 50 consistent with the requirements of particular surgical procedures. The cover of the expander conforms to the shape of the base.

After insertion of the expander and healing of the incision, fluid is injected into the interior chamber of the expander and the cover and overlying tissue are expanded as described previously.

Fourth Embodiment Adjustable Soft Tissue Expander

Figure 16:
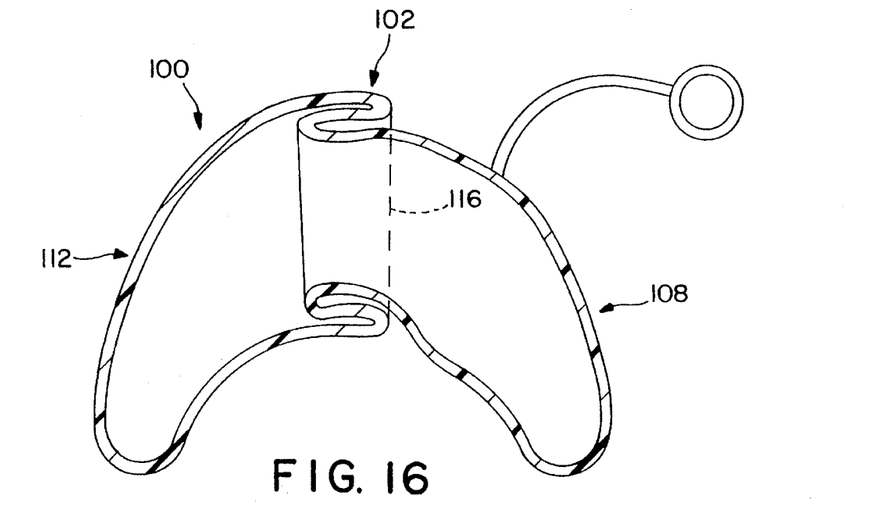
Figure 17:
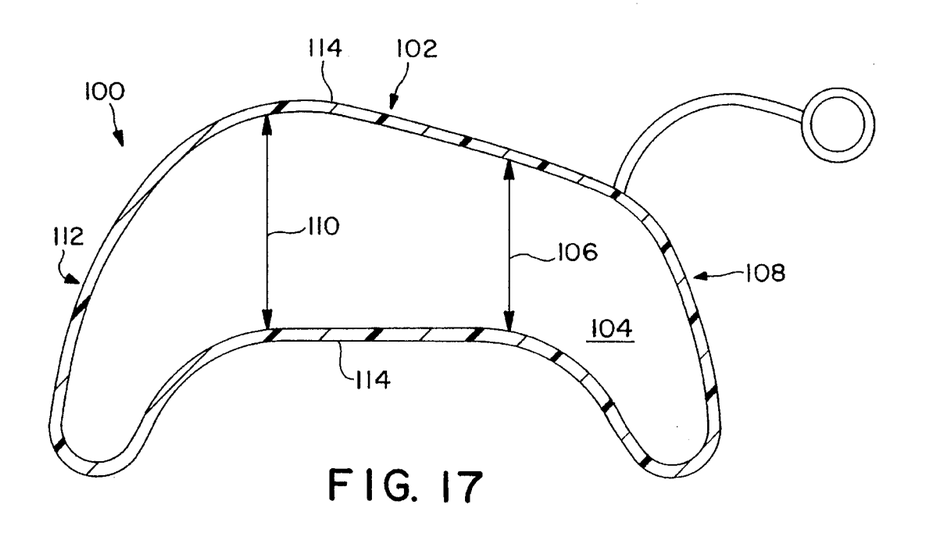

FIGS. 16 and 17 illustrate a fourth embodiment soft tissue expander 100 having a generally crescent shape. Expander 100 is like expander 50 with the exception that the tubular central portion 102 is tapered and the base 104 has a width 106 adjacent arm 108 less than the width of the base 110 adjacent the other arm 112. See FIG. 17. Widths 106 and 110 extend across the base to opposite sides of edge 114. A single deep S-shaped fold 116 is formed in the middle portion by inverting the narrow end of the middle portion into the wide end of the middle portion as shown in FIG. 16. The tapered central portion 102 facilitates folding the narrow width end into the wider width end to form the fold and is useful when difficulty is encountered in making the fold. Expander 100, when fully elongated as shown in FIG. 17, assumes the shape of a valise handle.

The area of base 104 of expander 10 is adjusted as previously described by varying the length or angle of fold 116 or, if required, by completely effacing the fold. Once the area of the base has been determined, the surgeon implants the expander and, after healing has been completed, the overlying cover (not illustrated) is expanded as previously described.

Fifth Embodiment Adjustable Soft Tissue Expander

Figure 18:
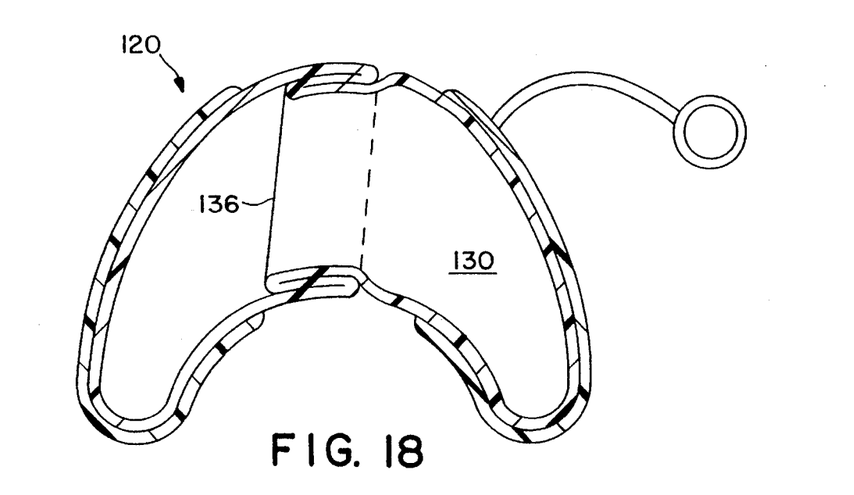
Figure 19:
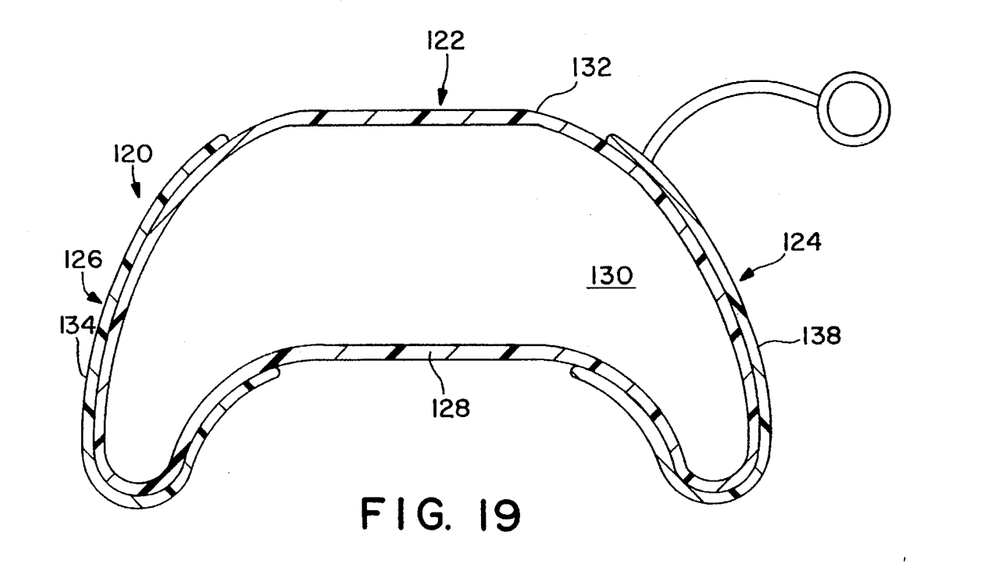

FIGS. 18 and 19 disclose a fifth embodiment adjustable soft tissue expander 120 similar to second embodiment expander 50. Expander 120 includes a single layer tubular central portion 122 and crescent arms 124 and 126 joined to the ends of the central portion. The expander includes a single layer of elastomer 128 extending completely around the base 130 and the cover (not illustrated) which joins the base at edge 132. Second elastomer layers 134 are formed on the outside of the first layer 128 on both arms 124 and 126. The central portion 122 of expander 120 is thinner than the arms 124 and 126 in order to facilitate inverting one end of the central portion into the other end to form S-shaped fold 136 shown in FIG. 18. The fold extends around the central portion and across both the cover and base.

The inner layer 128 of expander 120 may be relatively thin and possesses improved flexibility over the flexibility of the thicker two-layers arms 124 and 126. The flexibility of the inner portion facilitates forming the fold 136, adjustment of the shape of the base by varying the depth and angle of the fold, and expansion.

Prior to implantation of expander 120, a surgeon adjusts the shape of the expander base 130 by lengthening or foreshortening the fold, and rotating the arms relative to the middle portion or completely effacing the fold as required in order that the base assumes a proper shape for performing the desired soft tissue expansion. The expander with the base in the proper shape is then implanted and expanded as previously described. The cover overlying base 130 conforms to the shape of the base when implanted so that the expansion of overlying tissue is in part governed by the shape of the base.

FIG. 19 illustrates expander 120 in the fully elongated or extended position in which fold 136 is effaced and the expander assumes the shape of a valise handle.

Sixth Embodiment Adjustable Soft Tissue Expander

Figure 20:
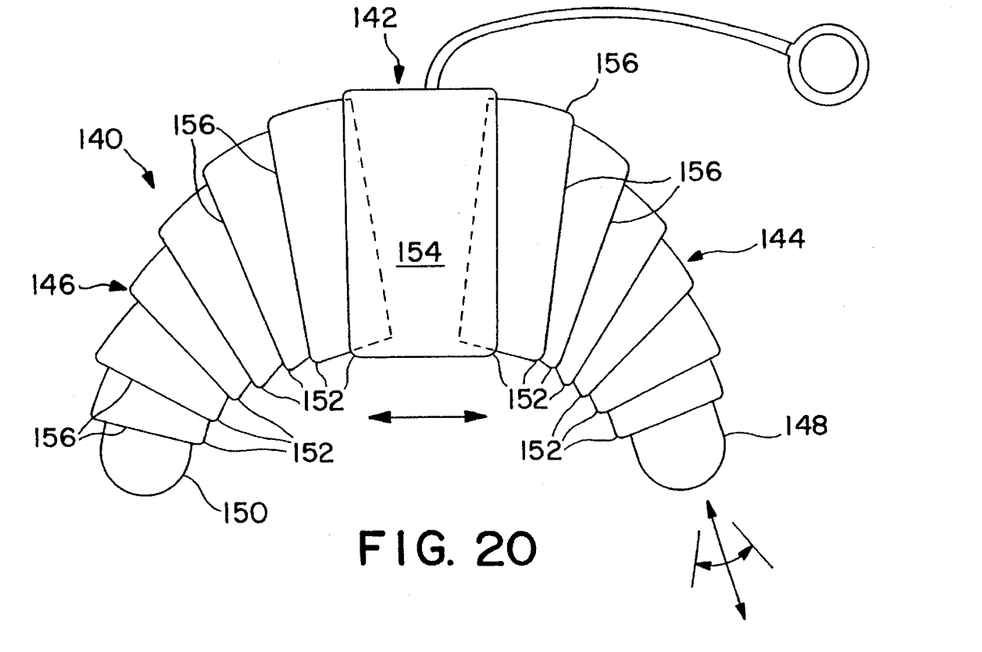
FIGS. 20–23 are top views of a sixth embodiment adjustable soft tissue expander in different positions.
Figure 21:
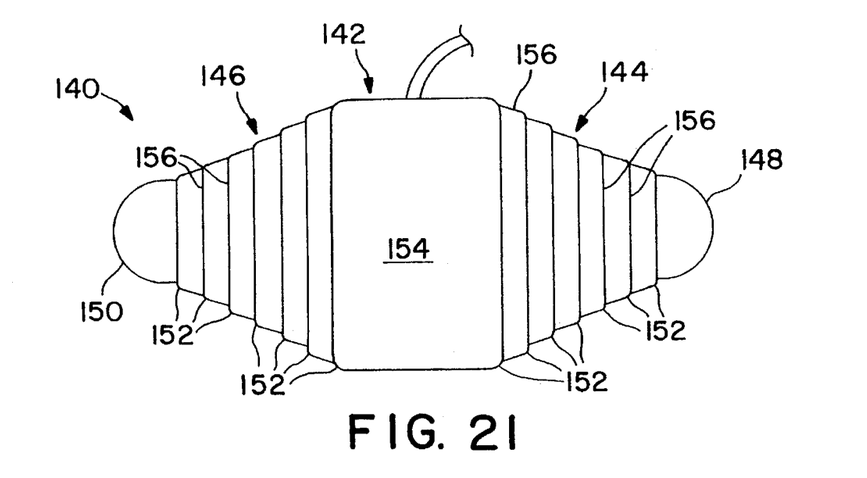

FIGS. 20–23 disclose a sixth embodiment adjustable soft tissue expander 140 including a tubular central portion 142, a pair of folded arms 144 and 146 each joining one end of the central portion, a base and an expandable cover. The arms include rounded closed ends 148 and 150 located away from the central portion. As illustrated in FIG. 21, the arms are tapered in width from a maximum width at central portion 142 to a minimum width at ends 148 and 150.

The expander 140 includes an inlet port and tube communicating the port to the interior chamber of the expander. The port and tube are similar to the ports and tubes previously described.

A plurality of circumferential S-shaped folds 152 are formed along the length of each arm 144 and 146 from the central portion 142 to ends 148 and 150. The folds overlap each other and extend across the width of the expander base (not illustrated) and across the width of the expander cover 154 and cross opposite sides of the circumferential edge 156 joining the base and cover. The folds are similar to the previously described folds and are formed by folding or inverting circumferential portions of the arms into portions located more closely adjacent the central portion 142. The outer edges 156 of the folds face away from the central portion.

The folded arms 144 and 146 of expander 140 are highly flexible and may be moved to change the shape of the base. This flexibility assures that a surgeon can vary the shape of the expander base by movement of the arms elongating or foreshortening the individual folds and rotating the folds or even by effacing one or more folds completely.

FIG. 20 illustrates both arms 144 and 146 bent downwardly so that the expander base assumes a crescent shape. If desired, the arms may be bent downwardly further to position ends 148 and 150 closer together than shown in FIG. 20. The arms may be elongated to position the ends further below the central portion. The arms may be shortened.

FIG. 21 illustrates both arms extended directly away from the central portion with ends 148 and 150 spaced a distance away from the ends of the central portion without rotating folds 152. If desired, the ends may be pulled further away from the central portion to elongate the arms and foreshorten the folds. The folds may be completely effaced to position the ends 148 and 150 a maximum distance away from the central portion.

Figure 22:
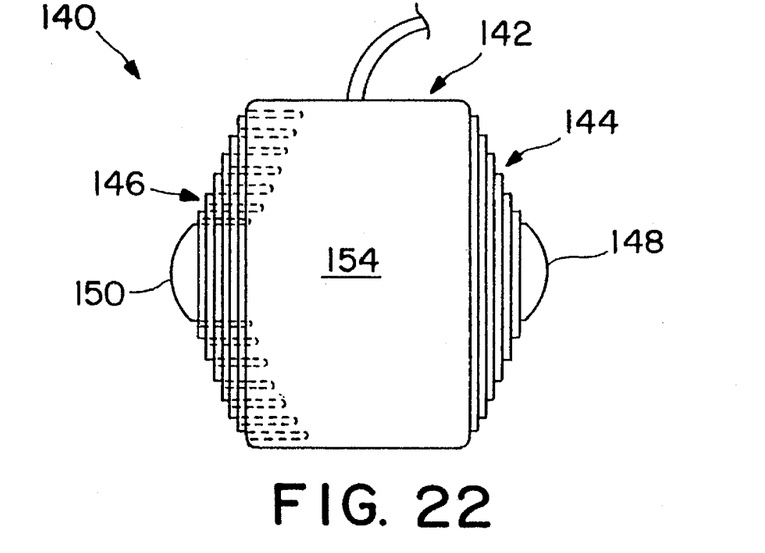

FIG. 22 illustrates the position of expander 140 in which the folds have been lengthened and the arms have been partially collapsed within the central portion.

Figure 23:
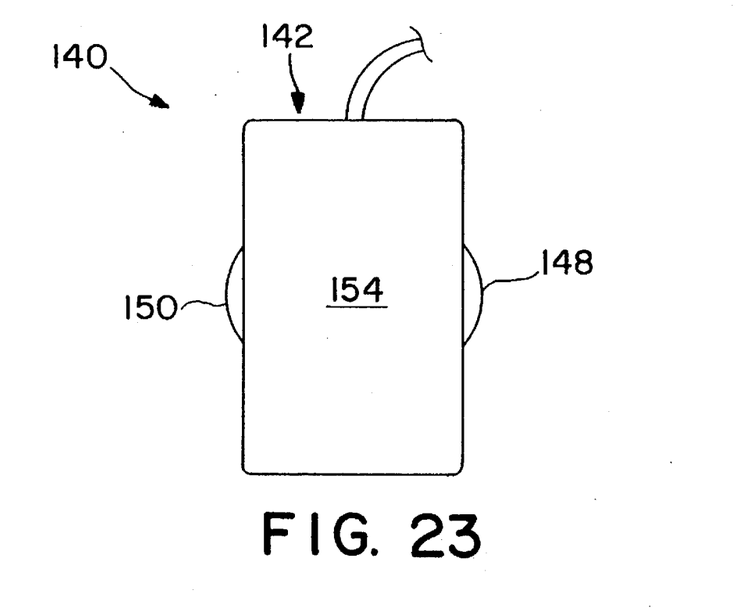

FIG. 23 illustrates the position of expander 140 in which the arms have been completely collapsed within the central portion with the tips of ends 148 and 150 extending short distances outwardly of the ends of the central portion.

The surgeon may adjust the shape of the base of expander 140 by varying the position of the arms 144 and 146 as required. The arms of expander 140, and the arms of the other disclosed expanders, need not be moved to symmetrical positions with regard to the central portion of the expander. For instance, one arm of expander 140 may be bent down and the other arm may be bent up so that the base of the expander assumes a sinuous or S-shape.

Prior to implantation of expander 140, the surgeon adjusts the base of the expander by moving arms 144 and 146 as required. The plural folds in the two arms permit the surgeon great flexibility in adjusting the shape of the base. If the arms are fully extended outwardly from the central portion, the base has a long and relatively narrow shape. If both arms are bent down from the central portion, the expander base assumes a narrow crescent shape. Other shapes are readily available, as previously described, Once the expander base has been adjusted as required, the expander is implanted below a skin layer and the incision is allowed to heal so that the base is held in the desired inserted shape. Fluid is injected into the interior cavity of the expander to expand the cover and overlying tissue as previously described.

Seventh Embodiment Dimensionally Adjustable Tissue Expander

Figure 24:
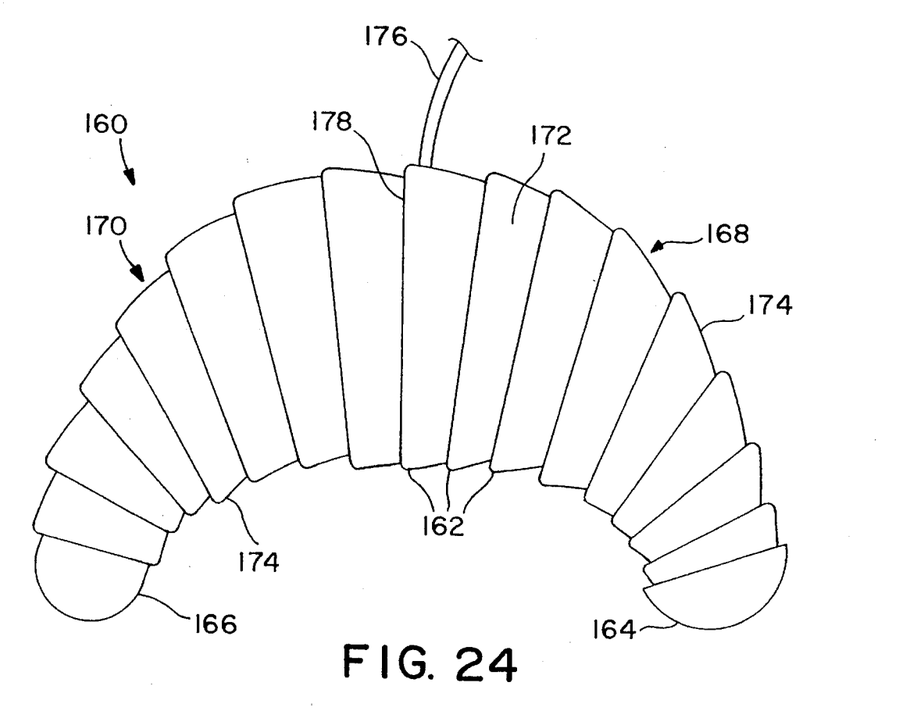
FIG. 24 is a top view of a seventh embodiment adjustable expander.

FIG. 24 illustrates a seventh embodiment soft tissue expander 160 similar to expander 140 with the exception that a plurality of like S-shaped overlapping folds 162 extend along the entire length of the expander between opposed closed ends 164 and 166. The expander 160 includes two folded arms 168 and 170. Each arm extends from a closed end 164, 166 to the wide central portion of the expander. The folds 162 extend circumferentially around the expander which includes a base (not illustrated) and an expandable cover 172 overlying the base and joined to the base at circumferential edge 174. An inlet port (not illustrated) is connected to one end of inlet tube 176 which opens through a wall of the expander to communicate the port with the interior chamber of the expander between the cover and base. The tube is preferably mounted on a fold adjacent an outer fold edge 178 to permit maximum foreshortening and lengthening of the fold during manipulation of the expander by the surgeon to adjust the shape of the expander base prior to implantation.

Expander 160 includes folds spaced along the entire length of the expander from end to end. The folds may be foreshortened or lengthened to adjust the shape of the expander base before implantation.

The folds in expander 160 all have outer edges 178 facing expander end 166 with multiple thickness fold layers. In this way, the double thickness fold layers in the expander all extend in the same direction and do not overlap each other.

The adjustability of the base of expander 160 is enhanced by providing folds of the same orientation along the entire length of the expander. Additionally, the expander does not include a fixed dimension central portion so that the base is provided with an additional degree of adjustability over the bases of the previously described expanders. The shape of the entire length of the base may be adjusted.

After adjustment of the shape of the base of expander 160 by the surgeon, the expander is positioned within a surgical incision. The incision is closed, healing occurs and the overlying skin tissue is expanded by injecting fluid into the cavity of the expander through tube 176 as previously described. The expandable cover 172 conforms in shape to the shape of the base, assuring that the overlying tissue layer is expanded above the base and assumes a desired shape.

Eighth Embodiment Dimensionally Adjustable Tissue Expander

FIG. 25 illustrates an eighth embodiment adjustable soft tissue expander 180 which is identical to the previously described soft tissue expander 10 shown in FIGS. 1 through 9 except that the parts of the expander base underlying the arms are reinforced. Expander 180 includes a cover 182, base 184 and edge 186. The cover and base define an inflatable interior chamber 188. The expander has a general crescent shape with a pair of tubular arms 190, 192 extending away from tubular central portion 194. A plurality of overlying S-shaped folds 196 extend around the central portion 194. The expander 180 includes a continuous layer of elastomer material defining the interior surface of chamber 188, like expander 10. Elements 182–194 correspond to like elements of expander 10.

Base 184 of expander 180 includes layers 198 of reinforced silicone elastomer material under arms 190 and 192. The reinforced layers 198 prevent the limited expansion of the portions of the base underlying the arms during expansion of the overlying cover and tissue layer. The reinforced layers 198 may be identical to the reinforced layers in the base of the expanders disclosed in Manders U.S. Pat. No. 4,574,780. The layers 198 assure that the portions of the base underlying the arms 190 and 192 are dimensionally stable during tissue expansion.

If desired, the bases of any of the disclosed adjustable soft tissue expanders may be provided with a layer of reinforced silicone elastomer to assure dimensional stability of the base during expansion. The layer may underlie the complete area of the base, including the fold or folds, or may underlie areas away from the folds. In expander 180, a single layer of reinforced silicone elastomer may be provided extending under both the arms and under the elastomer material forming the folds 196 in the central portion 194. In such case, the reinforced layer would be folded together with the overlying non-reinforced elastomer layer in the base.

All of the disclosed expanders include bases with S-shaped folds extending across the widths of the bases. The folds permit adjustment of the shape of the base by the surgeon prior to implantation. The adjustment is achieved by lengthening, foreshortening or rotating the folds. The folds also extend up into the covers from the bases and across the overlying covers to permit the covers to conform to the shape of the bases.

It is contemplated that the invention includes an expander having a base with a S-shaped fold extending inwardly from an edge of the base to permit adjusting the shape of the base and with a cover joining the edge of the base with sufficient compliance at the fold in the base so that the cover conforms to the adjusted shape of the base. The cover may be formed from very thin, highly compliant elastomer material and need not include a fold or folds which extend up from the base and entirely across the cover to an opposite edge of the base. The invention includes an expander in which the fold or folds in the base end in a fold or folds extending a short distance from the edge into the cover. These folds facilitate dimensional flexibility at the cover to permit the surgeon to adjust the shape of the base as required.

As illustrated in the drawings, the folds may overlap each other and lie flat with adjacent sides resting flat on each other nearly parallel to the wall of the expander. Alternatively, the folds may extend generally perpendicular to the wall of the expander to form vertical corrugations of the type shown in FIGS. 8 and 9.

The bases of the expanders disclosed herein are all disclosed as being flat. Expanders are commonly manufactured with flat bases. In practice, expanders are inserted in incisions or pockets made below curved skin layers where the bases of the inserted expanders are curved and not flat. Expanders may be made with curved, non-flat bases for insertion into curved pockets.

While we have illustrated and described preferred embodiments of our invention, it is understood that this is capable of modification, and we therefore do not wish to be limited to the precise details set forth, but desire to avail ourselves of such changes and alterations as fall within the purview of the following claims.

What we claim as our invention is:

1. A dimensionally adjustable tissue expander adapted to be inserted under soft tissue to be expanded, the expander comprising a substantially flat base having a shape and defining a peripheral edge; a cover formed from an expandable elastomer, the cover overlying the base and joined to the base at the peripheral edge to define a closed interior chamber; a movable S-shaped fold in the base having a number of adjustable shapes; and a port for inflating and deflating the chamber, said fold being freely movable to vary the shape of the base.

2. An expander as in claim 1 wherein said fold is located adjacent the peripheral edge.

3. An expander as in claim 1 including a first plurality of overlapping S-shaped folds in the base, all of said folds extending in the same direction.

4. An expander as in claim 3 including a second plurality of overlapping S-shaped folds, all of said second folds extending in a direction opposite the direction of said first folds.

5. An expander as in claim 1 wherein the base is elongate and defines opposed ends, and including a plurality of overlapping folds extending from one end of the base to the other end of the base, all of said folds extending in the same direction.

6. A dimensionally adjustable tissue expander comprising a substantially flat base defining a peripheral edge; a cover formed from an expandable elastomer, the cover overlying the base and joined to the base at the peripheral edge to define a closed interior chamber; a fold extending from the peripheral edge a distance into the base and a distance into the cover; and a port for inflating and deflating the chamber, said fold being freely movable to adjust the shape of the base to a selected shape for expansion of a soft tissue layer overlying the cover the base having sufficient compliance to insure that the base retains the selected shape from implantation of the expander into a surgically-formed incision until tissue surrounding the expander base heals.

7. An expander as in claim 6 wherein said fold extends from the peripheral edge on one side of the base across the base to the peripheral edge on the opposite side of the base.

8. An expander as in claim 6 including a plurality of overlapping folds in the base.

9. An expander as in claim 8 wherein said base is elongate, the expander including opposed ends and said folds are spaced along the length of the expander.

10. A dimensionally adjustable tissue expander comprising a substantially flat base defining a peripheral edge; a cover formed from an expandable elastomer, the cover overlying the base and joined to the peripheral edge of the base to define a closed interior chamber; the base including a freely movable dimensionally adjustable fold having a number of adjustable shapes; the expander including a central portion, and opposed arms to either side of the central portion and a port for inflating and deflating the chamber, said fold being freely movable to adjust the shape of the base to a selected shape for expansion of a soft tissue layer overlying the cover, the base having sufficient compliance to insure that the base retains the selected shape from implantation of the expander into a surgically-formed incision until tissue surrounding the expander base heals.

11. An expander as in claim 10 wherein the fold extends circumferentially around the expander.

12. An expander as in claim 10 including folds extending around each of said arms and all folds on each arm are oriented in the same direction.

13. An expander as in claim 12 wherein said central portion is generally rectangular.

14. An expander as in claim 10 wherein the fold extends around the central portion.

15. An expander as in claim 14 wherein said central portion is tapered.

16. An expander as in claim 14 wherein the material forming the central portion is thinner than the material forming the arms.

17. An expander as in claim 14 wherein the expander has the shape of a valise handle when fully elongated.

18. A dimensionally adjustable tissue expander adapted to be implanted under soft tissue to be expanded, the expander comprising a substantially flat imperforate base, the base defining a peripheral edge; an expandable imperforate cover formed of compliant material overlying the base and joined to the base at the peripheral edge to form a closed interior chamber between the cover and base; a port opening into the chamber to permit fluid to be injected into the chamber and to be withdrawn from the chamber; and a first adjustable fold in the base.

19. An expander as in claim 18 wherein said fold extends to the edge.

20. An expander as in claim 19 wherein said fold extends past the edge and into the cover.

21. An expander as in claim 19 wherein said fold extends across the base between opposed sides of the peripheral edge.

22. An expander as in claim 21 wherein said fold extends circumferentially around the expander.

23. An expander as in claim 18 including a plurality of adjustable folds in the base.

24. An expander as in claim 23 wherein said folds overlie each other.

25. An expander as in claim 23 wherein said folds are spaced from each other.

26. An expander as in claim 18 including a second fold in the base spaced from said first fold and the base includes a non-adjustable portion between the folds.

27. An expander as in claim 26 wherein the expander includes a pair of arms and a plurality of overlapping folds on each arm.

28. An expander as in claim 18 wherein the base is elongate and includes opposed ends and including a plurality of folds spaced along the base from one end of the base to the other end of the base.

29. An expander as in claim 28 wherein the folds overlie each other and are oriented in the same direction.

30. An expander as in claim 18 including a tubular central portion, a pair of tubular arms each located to one side of the central portion, said arms being tapered from a maximum width at the central portion to a minimum width at the ends of the arms, said fold being located in the central portion of the base.

31. An expander as in claim 30 wherein the fold extends circumferentially around the expander.

32. An expander as in claim 31 wherein the material forming the fold is thinner than the material forming the arms.

33. An expander as in claim 30 including a plurality of folds in the central portion of the base.

34. An expander as in claim 33 wherein the folds extend around the central portion.

35. An expander as in claim 30 wherein the arms are curved and both ends are located to one side of the central portion so that the expander has a crescent shape and a valise handle shape when fully elongated.

36. An expander as in claim 35 wherein said central portion is thinner than said arms.

37. An expander as in claim 30 wherein said central portion is tapered.

38. An expander as in claim 20 including a tapered tubular arm and an adjustable fold extending around the arm.

39. An expander as in claim 38 including a plurality of overlapping folds on the arm.

40. An expander as in claim 18 wherein said fold is S-shaped.

* * * * *